United States Patent
Kakehashi (10) Patent No.: US 9,872,607 B2
(45) Date of Patent: Jan. 23, 2018

(54) ENDOSCOPE

(71) Applicant: OLYMPUS CORPORATION, Tokyo (JP)

(72) Inventor: Taigo Kakehashi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/162,755

(22) Filed: May 24, 2016

(65) Prior Publication Data

US 2016/0262595 A1 Sep. 15, 2016

Related U.S. Application Data

(63) Continuation of application No. PCT/JP2015/065087, filed on May 26, 2015.

(30) Foreign Application Priority Data

Jun. 9, 2014 (JP) .................. 2014-118805

(51) Int. Cl.
*A61B 1/00* (2006.01)
*A61B 1/005* (2006.01)
(Continued)

(52) U.S. Cl.
CPC ............ *A61B 1/0055* (2013.01); *A61B 1/005* (2013.01); *A61B 1/0052* (2013.01);
(Continued)

(58) Field of Classification Search
CPC ..... A61B 1/0052; A61B 1/0055; A61B 1/057; A61B 1/0607; A61M 25/0012;
(Continued)

(56) References Cited

U.S. PATENT DOCUMENTS

2001/0047124 A1 11/2001 Yamamoto
2004/0242966 A1* 12/2004 Barry .................. A61B 1/0055
600/146
(Continued)

FOREIGN PATENT DOCUMENTS

EP 1820457 A1 8/2007
EP 2612608 A1 7/2013
(Continued)

OTHER PUBLICATIONS

International Search Report dated Aug. 25, 2015 issued in PCT/JP2015/065087.

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

An endoscope includes: a bending portion, a wire, and a coil sheath, including a single element wire, an outer peripheral face of which is formed to be a curved face on one side of the outer peripheral face and to be a flat surface on another side of the outer peripheral face, the coil sheath being passed inside by the wire and configured by being helically wound by the element wire along a longitudinal direction such that the outer peripheral face formed to be the curved face and the outer peripheral face formed to be the flat surface are in contact with each other.

7 Claims, 8 Drawing Sheets (51) Int. Cl.
  *A61M 25/00* (2006.01)
  *F16L 11/10* (2006.01)
  *A61B 1/06* (2006.01)
  *G02B 23/24* (2006.01)
  *A61M 25/09* (2006.01)

(52) U.S. Cl.
  CPC ........ *A61B 1/0057* (2013.01); *A61B 1/00071* (2013.01); *A61B 1/0607* (2013.01); *A61M 25/0045* (2013.01); *F16L 11/10* (2013.01); *G02B 23/2476* (2013.01); *A61M 25/005* (2013.01); *A61M 25/0012* (2013.01); *A61M 2025/09066* (2013.01)

(58) Field of Classification Search
  CPC ............ A61M 25/0045; A61M 25/005; A61M 25/0052; A61M 2025/09066; F16L 11/081; F16L 11/088; F16L 11/10; F16L 11/115

USPC .................................................. 138/129, 144
  See application file for complete search history.

(56) References Cited

U.S. PATENT DOCUMENTS

2006/0271066 A1  11/2006  Kimura et al.
2013/0190560 A1  7/2013  Kaneko et al.

FOREIGN PATENT DOCUMENTS

| | | | |
|---|---|---|---|
| JP | H04-051929 A | 2/1992 | |
| JP | 2001-321386 A | 11/2001 | |
| JP | 2006-158668 A | 6/2006 | |
| JP | 2006-230635 A | 9/2006 | |
| JP | 2011-120687 A | 6/2011 | |
| WO | WO 2006/062020 A1 | 6/2006 | |
| WO | WO2013/038813 * | 3/2013 | .......... A61M 25/005 |
| WO | WO 2013/038813 A1 | 3/2013 | |

* cited by examiner

ENDOSCOPE

CROSS REFERENCE TO RELATED APPLICATION

This application is a continuation application of PCT/JP2015/065087 filed on May 26, 2015 and claims benefit of Japanese Application No. 2014-118805 filed in Japan on Jun. 9, 2014, the entire contents of which are incorporated herein by this reference.

BACKGROUND OF THE INVENTION

1. Field of the Invention

The present invention relates to an endoscope including a bending portion that operates upon the bending portion being pulled.

2. Description of the Related Art

In recent years, medical devices to be inserted into a subject, for example, endoscopes, have been widely used in a medical field. An elongated insertion portion of an endoscope is inserted into a subject, enabling, e.g., observation and/or treatment of a site to be examined inside the subject.

Here, a configuration in which an actuating member, for example, a bending portion that is bendable in a plurality of directions is provided in the insertion portion of the endoscope is publicly known.

The bending portion is capable of, in addition to enhancement in capability of forward movement of the insertion portion in a flexed part in a duct, changing an observation direction of an observation optical system provided in a distal end portion provided so as to be continuous with a distal end in a longitudinal axis direction of the insertion portion (hereinafter simply referred to as "distal end") of the bending portion in the insertion portion.

Typically, the bending portion includes a plurality of bending pieces joined along the longitudinal axis direction of the insertion portion and is thereby bendable in, for example, four directions: upward, downward, rightward and leftward.

More specifically, the bending portion is configured so as to be bendable in any of the upward, downward, rightward and leftward directions as a result of a corresponding one of four wires, each being inserted inside the insertion portion so as to be movable forward and backward in the longitudinal axis direction and including a distal end fixed to a bending piece positioned furthest on the distal end side in the longitudinal axis direction (hereinafter simply referred to as "distal end side") from among the plurality of bending pieces, being pulled using an operation input section of an operation portion.

Also, in the insertion portion, a flexible tube that has flexibility and is elongated in a longitudinal axis direction is provided so as to be continuous with a proximal end in a longitudinal axis direction (hereinafter simply referred to as "proximal end") of the bending portion.

Here, Japanese Patent Application Laid-Open Publication No. 2011-120687 discloses a configuration in which four wires are respectively inserted inside four coil sheaths, each including an element wire closely wound in a helical fashion along a longitudinal axis direction, inside a flexible tube and a distal end of each coil sheath is fixed to a distal end of the flexible tube and a proximal end of each coil sheath is fixed inside an operation portion.

The respective coil sheaths guide the respective wires in such a manner that the respective wires are movable along the longitudinal axis direction without deviating in a radial direction or a circumferential direction of the flexible tube. Also, each coil sheath has a function that, upon the bending portion being bent as a result of each corresponding wire being pulled, prevents even the flexible tube from bending together with the bending portion because of compression of the relevant coil sheath in the longitudinal axis direction due to the fixation of the distal end and the proximal end.

Figure 13:
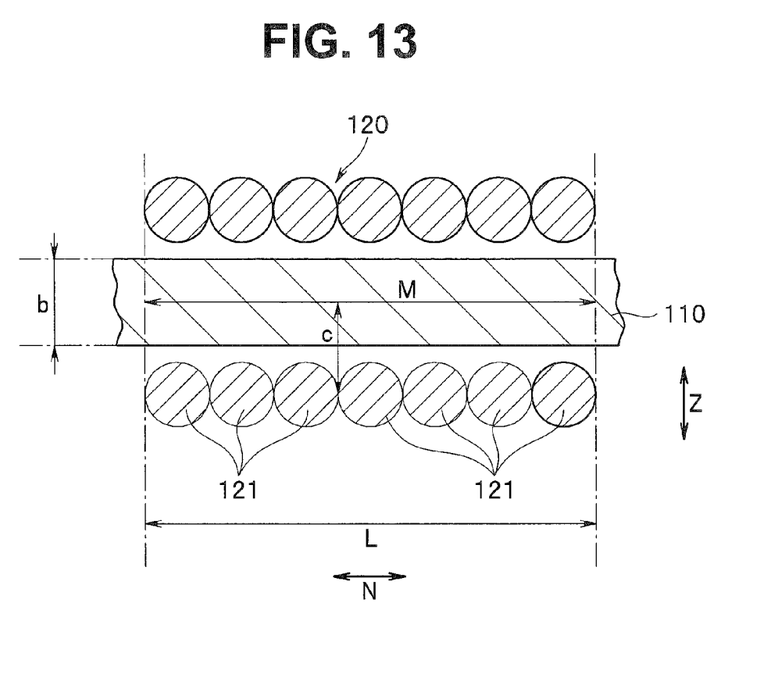
FIG. 13 is a partial cross-sectional view illustrating a state in which a wire is inserted inside a conventional coil sheath and including a longitudinal axis direction of the wire.
Figure 14:
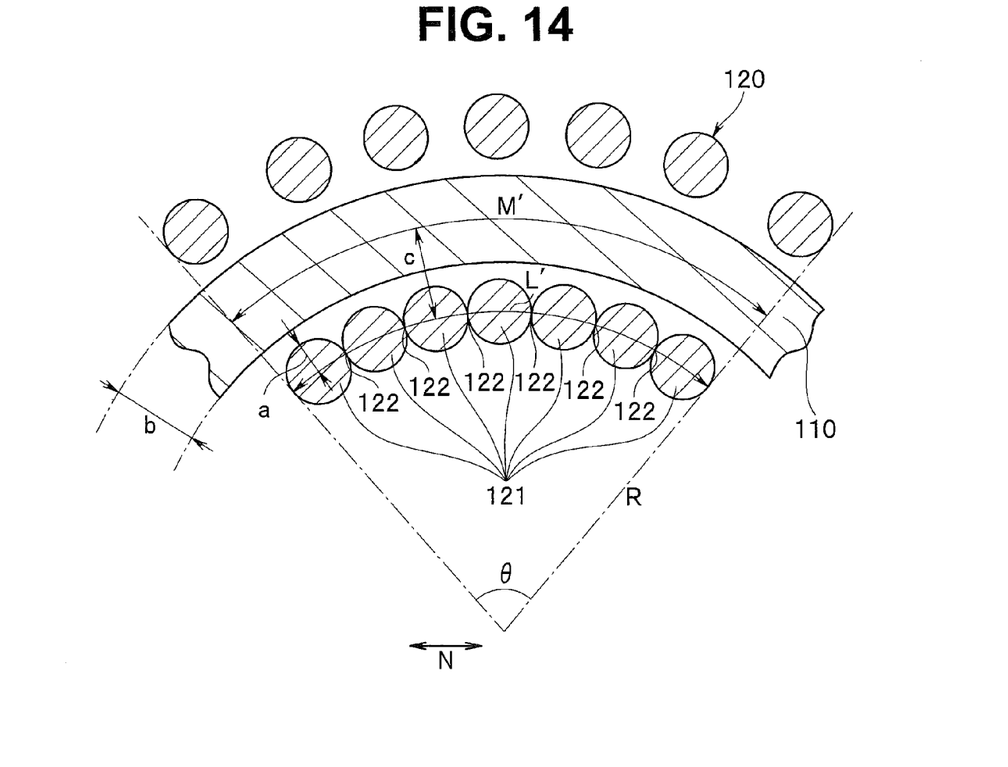
FIG. 14 is a partial cross-sectional view illustrating a state in which the coil sheath in FIG. 13 is bent and the wire is thereby drawn into the coil sheath and including the longitudinal axis direction of the wire.

FIG. 13 is a partial cross-sectional view illustrating a state in which a wire is inserted inside a conventional coil sheath and including a longitudinal axis direction of the wire, and FIG. 14 is a partial cross-sectional view illustrating a state in which the coil sheath in FIG. 13 is bent and the wire is thereby drawn into the coil sheath and including the longitudinal axis direction of the wire.

Upon an insertion portion being inserted into a subject, a flexible tube passively bends along a shape of the inside of the subject because of flexibility of the flexible tube. As a result of the bending of the flexible tube, a coil sheath 120 provided inside the flexible tube bends as illustrated in FIG. 14 from a linear state along a longitudinal axis direction N, which is illustrated in FIG. 13.

Here, where the coil sheath 120 bends, a wire 110 inserted inside the coil sheath 120 may be drawn into the coil sheath 120 by the amount of the bending of the coil sheath 120.

More specifically, as illustrated in FIG. 13, where L is a length in the longitudinal axis direction N of a predetermined area of the coil sheath 120 and M is a length in the longitudinal axis direction N of the wire 110 inserted inside the coil sheath 120 in the length L, as illustrated in FIG. 14, if the coil sheath 120 bends, the wire 110 may elastically deform because the wire 110 extends by the amount of M'−M.

Still more specifically, an amount of the wire 110 drawn in upon bending of the coil sheath 120 in the predetermined area L is defined by a distance a from a line connecting contact points 122 between respective parts of an element wire 121 included in the coil sheath 120 to an outer peripheral face of the element wire 121, a diameter b of the wire 110, a bending angle θ of the coil sheath 120 and a radius R of curve of a part on the inner side in the bending direction of the coil sheath 120.

This is because, since a length L' of the part on the inner side in the bending direction of the coil sheath 120 after the coil sheath 120 bending is L'=2πR×θ/360 and the length M' of the wire 110 after the elastic deformation is M'=2π(R+a+b/2)×θ/360, the amount of the wire 110 drawn in can be defined by M'−L'=(2π(R+a+b/2)−2πR)×θ/360=πθ(a+b/2)/180.

Also, upon the wire 110 being pulled in order to bend the bending portion, the wire 110 is brought into contact with the part on the inner side in the bending direction of the coil sheath 120.

However, when the wire 110 is elastically deformed and the coil sheath 120 is bent as illustrated in FIG. 14, frictional resistance of the wire 110 against the part on the inner side in the bending direction of coil sheath 120 sometimes becomes large compared to the case where the wire 110 is not elastically deformed and the coil sheath 120 is not bent as illustrated in FIG. 13, which results in increase in amount of strength of pulling the wire 110.

SUMMARY OF THE INVENTION

An endoscope according to an aspect of the present invention includes: a bendable bending portion; a wire to be pulled for bending the bending portion; and a coil sheath, including a single element wire, an outer peripheral face of which is formed to be a curved face on one side of the outer peripheral face and to be a flat surface on another side of the outer peripheral face, the coil sheath being passed inside by the wire and configured by being helically wound by the element wire along a longitudinal direction of the wire such that the outer peripheral face formed to be the curved face and the outer peripheral face formed to be the flat surface are in contact with each other.

DETAILED DESCRIPTION OF THE PREFERRED EMBODIMENTS

Embodiments of the present invention will be described below with reference to the drawings. It should be noted that the drawings are schematic ones and, e.g., a relationship between a thickness and a width of each member and ratios in thickness among the respective members are different from actual ones, and it should be understood that parts that are different in dimensional relationship and ratio depending on the drawings are included in the drawings.

(First Embodiment)

Figure 1:
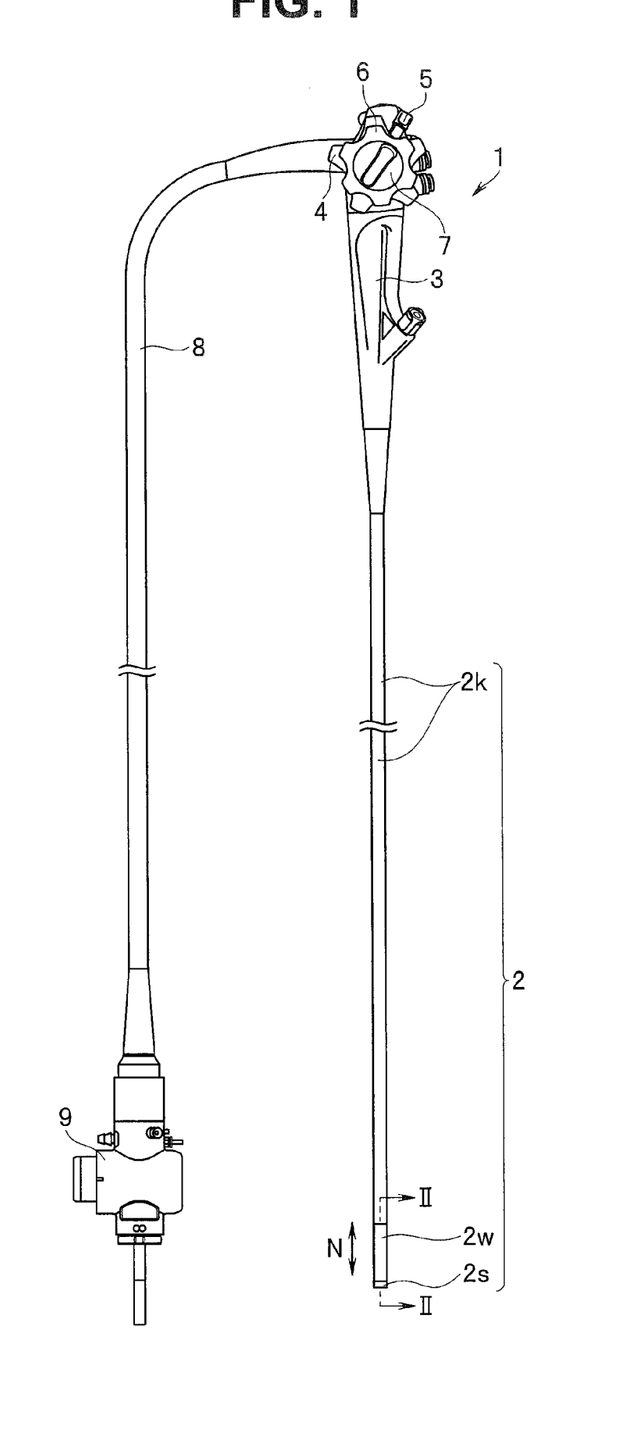
FIG. 1 is a diagram illustrating an outer appearance of an endoscope according to a first embodiment.

FIG. 1 is a diagram illustrating an outer appearance of an endoscope according to the present embodiment.

As illustrated in FIG. 1, a major part of an endoscope 1 includes an insertion portion 2 to be inserted into a subject, an operation portion 3 provided so as to be continuous with a proximal end of the insertion portion 2, a universal cord 8 extending out from the operation portion 3, and a connector 9 provided at an end of the extension of the universal cord 8. Note that the endoscope 1 is electrically connected to external apparatuses such as a control apparatus and an illumination apparatus via a connector 9.

A major part of the insertion portion 2 includes an elongated flexible tube 2k extending along a longitudinal axis direction N of the insertion portion 2, a bending portion 2w, which is an actuating member provided so as to be continuous with a distal end of the flexible tube 2k, and a distal end portion 2s provided so as to be continuous with a distal end of the bending portion 2w.

Inside the distal end portion 2s, e.g., a non-illustrated image pickup unit that picks up an image of the inside of the subject and a non-illustrated illumination unit that supplies illuminating light to the inside of the subject are provided.

The bending portion 2w is bendable in, for example, four directions: upward, downward, rightward and leftward, via later-described bending operation knobs 4 and 6 provided at the operation portion 3.

More specifically, at the operation portion 3, the bending operation knob 4, which is an operation input section for bending the bending portion 2w upward/downward, and the bending operation knob 6, which is an operation input section for bending the bending portion 2w rightward/leftward, are provided.

Also, inside the operation portion 3, a non-illustrated upward/downward bending pulley that, upon the pulley being rotated together with the bending operation knob 4, pulls/loosens later-described wires 10u and 10d (see FIG. 2) inserted inside the insertion portion 2 and the operation portion 3 and thereby bends the bending portion 2w upward/downward is provided.

Furthermore, inside the operation portion 3, a rightward/leftward bending pulley that, upon the pulley being rotated together with the bending operation knob 6, pulls/loosens later-described wires 10r and 10l (see FIG. 2. The wire 10r is not illustrated) inserted inside the insertion portion 2 and the operation portion 3 and thereby bends the bending portion 2w rightward/leftward is provided.

Note that since configurations of the upward/downward bending pulley and the rightward/leftward bending pulley are publicly known, detailed description thereof using the drawings will be omitted.

Also, at the operation portion 3, a fixing lever 5 for fixing a rotational position of the bending operation knob 4 is provided, and a fixing knob 7 for fixing a rotational position of the bending operation knob 6 is provided.

Next, a configuration of the major part according to the present embodiment on the distal end side of the insertion portion in FIG. 1 will be described with reference to FIG. 2. FIG. 2 is a partial cross-sectional view of the insertion portion along line II-II in FIG. 1.

Figure 2:
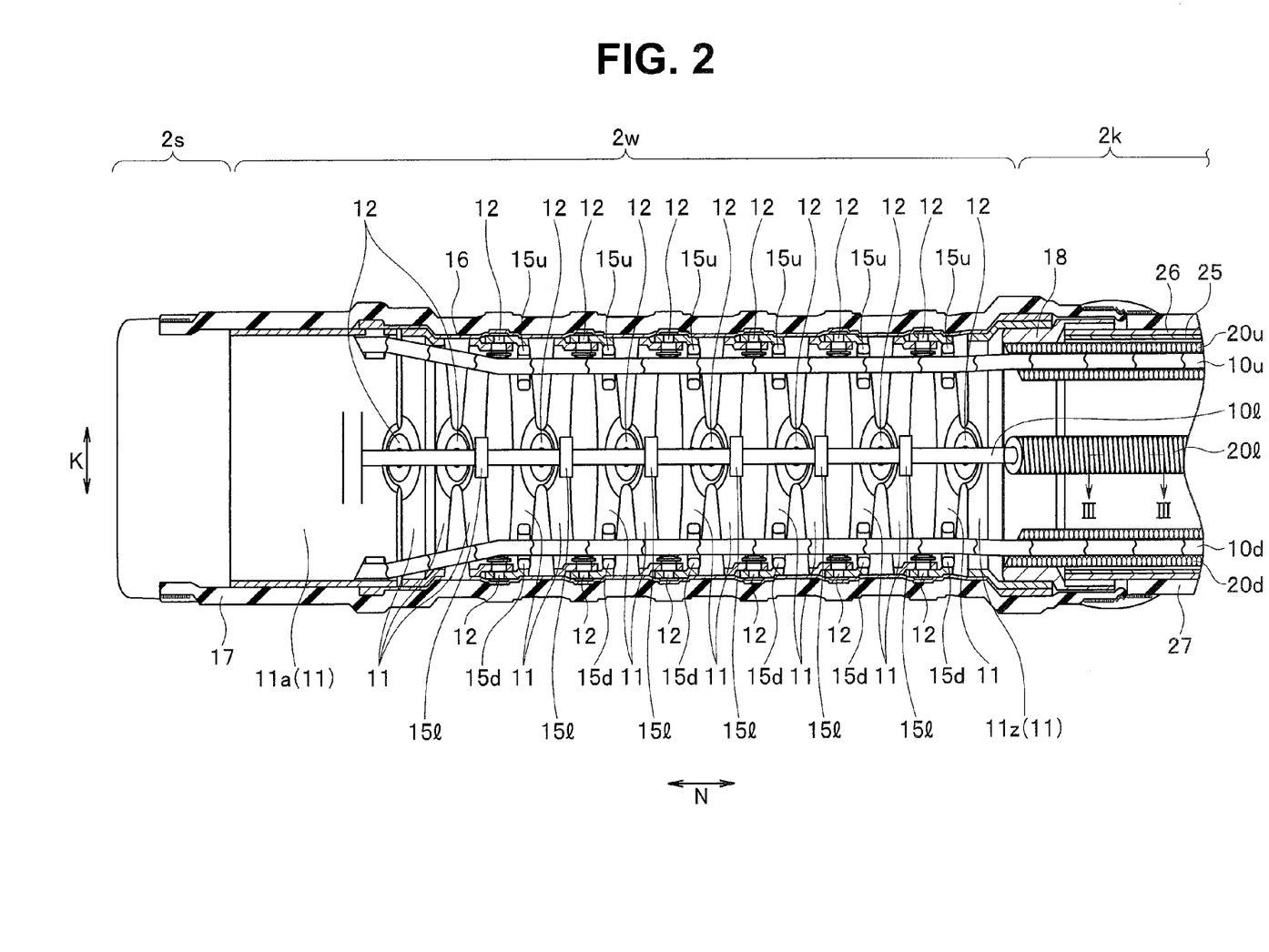
FIG. 2 is a partial cross-sectional view of an insertion portion along line II-II in FIG. 1.

As illustrated in FIG. 2, inside the bending portion 2w, a plurality of cylindrical bending pieces 11 are provided in such a manner that the bending pieces 11 are joined along the longitudinal axis direction N. Here, the plurality of bending pieces 11 are pivotally joined to respective pieces that are adjacent to the bending pieces 11 in the longitudinal axis direction N via respective rivets 12 so as to be bendable in four directions: upward, downward, rightward and leftward.

An outer periphery of the plurality of bending pieces 11 is covered by a braid 16 and an outer periphery of the braid 16 is covered by bending rubber 17.

Inside the insertion portion 2 and the operation portion 3, for example, four wires 10r, 10l, 10u and 10d (the wire 10r is not illustrated) for actuating, that is, bending the bending portion 2w, the wires 10r, 10l, 10u and 10d being movable forward/backward in the longitudinal axis direction N (hereinafter simply referred to as forward/backward), are inserted in such a manner that the wires 10r, 10l, 10u and 10d are shifted from one another by substantially 90° in a circumferential direction of the insertion portion 2.

A distal end of each of the wires 10r to 10d is fixed to a bending piece 11a positioned furthest on the distal end side from among the plurality of bending pieces 11 provided inside the bending portion 2w.

Also, a plurality of tubular guides 15r, 15l, 15u and 15d (the guide 15r is not illustrated) are fixed to an inner peripheral face of each bending piece 11, the guides 15r, 15l, 15u and 15d holding the respective wires 10r to 10d so that the wires 10r to 10d extend along the inner peripheral face of each bending piece 11 and are positioned substantially 90° shifted from one another in the circumferential direction.

More specifically, the guides 15r to 15d are also fixed substantially 90° shifted from one another in the circumferential direction. Also, the wire 10r is inserted inside the plurality of guides 15r, the wire 10l is inserted inside the plurality of guides 15l, the wire 10u is inserted inside the plurality of guides 15u, and the wire 10d is inserted inside the plurality of guides 15d.

Note that respective proximal ends of the two wires 10u and 10d for upward/downward bending are wound around the above-described upward/downward bending pulley, and respective proximal ends of the two wires 10r and 10l for rightward/leftward bending are wound around the above-described rightward/leftward bending pulley.

In other words, upon the bending operation knob 4 being operated, one of the two wires 10u and 10d for upward/downward bending is moved backward in the longitudinal axis direction N and the other is moved forward in the longitudinal axis direction N by the upward/downward bending pulley, that is, the one is pulled and the other is loosened, whereby the bending portion 2w bends either upward or downward.

Also, upon the bending operation knob 6 being operated, one of the two wires 10r and 10l for rightward/leftward bending is moved backward in the longitudinal axis direction N and the other is moved forward in the longitudinal axis direction N by the rightward/leftward bending pulley, that is, the one is pulled and the other is loosened, whereby the bending portion 2w bends either rightward or leftward.

Also, the distal end side of a joining member 18 is fixed to an inner periphery of a bending piece 11z positioned furthest on the proximal end side from among the bending pieces 11, and the distal end side of a braid included in the flexible tube 2k is fixed to an inner periphery on the proximal end side of the joining member 18.

Note that the braid includes a helical tube 25 including, for example, a metal and a reticular tube 26 covering an outer periphery of the helical tube 25, and an outer periphery of the reticular tube 26 is covered by an outer coat tube 27.

Also, respective outer peripheries of the four wires 10r to 10d inserted inside the flexible tube 2k are covered by respective coil sheaths 20r, 20l, 20u and 20d (the coil sheath 20r is not illustrated) that are, for example, flexible and elongated along the longitudinal axis direction N.

In other words, inside the flexible tube 2k, each of the four coil sheaths 20r to 20d is inserted at respective positions that are shifted from one another by substantially 90° in a circumferential direction of the flexible tube 2k.

Also, distal ends of the respective coil sheaths 20r to 20d are respectively fixed to the distal end of the flexible tube 2k, more specifically, to the joining member 18 via, for example, brazing. Furthermore, proximal ends of the respective coil sheaths 20r to 20d are fixed inside the operation portion 3.

Each of the coil sheaths 20r to 20d has a function that upon the bending portion 2w being bent as a result of each corresponding wire 10r to 10d being pulled, prevents even the flexible tube 2k from bending together with the bending portion 2w because of compression of the relevant coil sheath in the longitudinal axis direction N due to the fixation of the distal end and the proximal end.

Note that the coil sheaths 20r to 20d each include, for example, a closely-wound stainless steel coil, which is a flexible material.

The respective coil sheaths 20r to 20d include a flexible coil pipe because if the outer peripheries of the respective wires 10r to 10d are covered by, for example, a rigid pipe of a metal, the flexibility of the flexible tube 2k decreases.

Therefore, a member included in each of the coil sheaths 20r to 20d is not limited to a coil and any member can be employed as long as the member that prevents decrease in flexibility of the flexible tube 2k and can resist a compressing force exerted along the longitudinal axis direction N of the relevant one of the coil sheaths 20r to 20d upon the bending portion 2w being bent.

Next, a shape of an element wire of each of the coil sheaths 20r to 20d will be described with reference to FIGS. 3 to 6.

Figure 3:
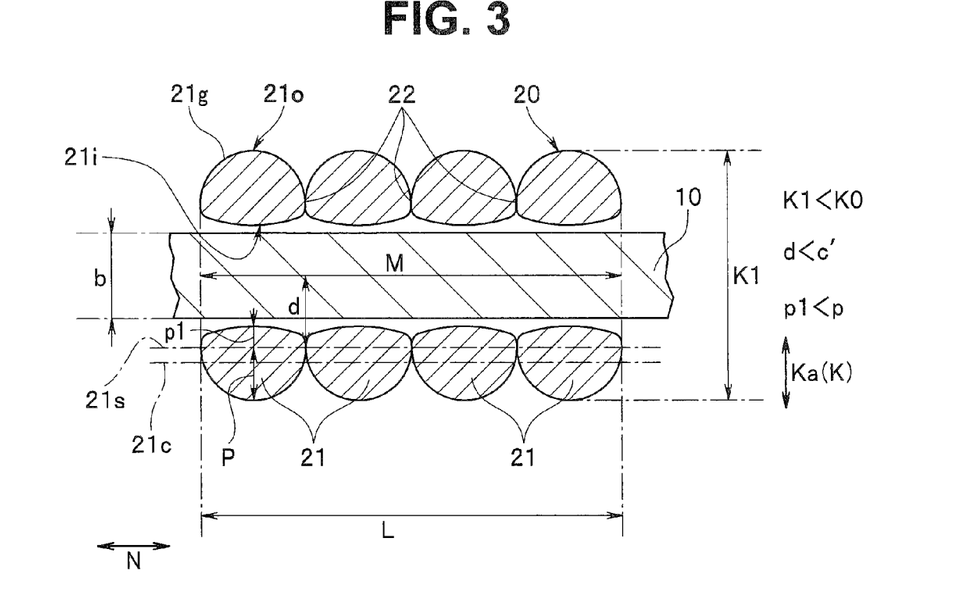
FIG. 3 is a partial cross-sectional view along line III-III in FIG. 2, including a coil sheath and a longitudinal axis direction of a wire.
Figure 4:
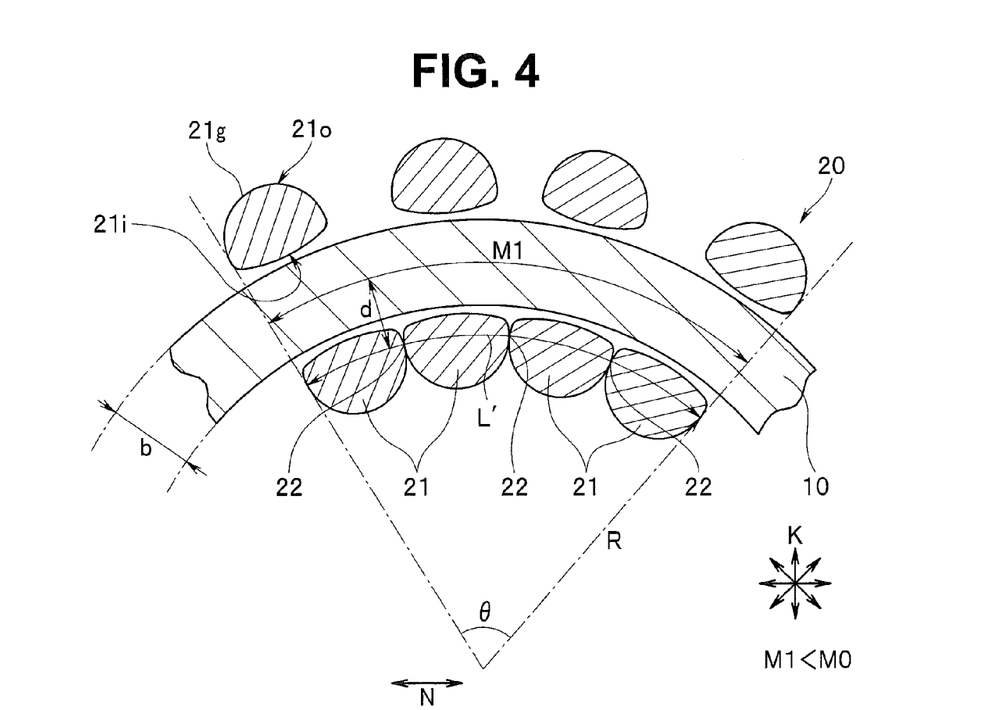
FIG. 4 is a partial cross-sectional view illustrating a state in which the coil sheath in FIG. 3 is bent and the wire is thereby drawn into the coil sheath and including the longitudinal axis direction of the wire.

FIG. 3 is a partial cross-sectional view along line III-III in FIG. 2, including a coil sheath and a longitudinal axis direction of a wire, and FIG. 4 is a partial cross-sectional view illustrating a state in which the coil sheath in FIG. 3 is bent and the wire is thereby drawn into the coil sheath and including the longitudinal axis direction of the wire.

Figure 5:
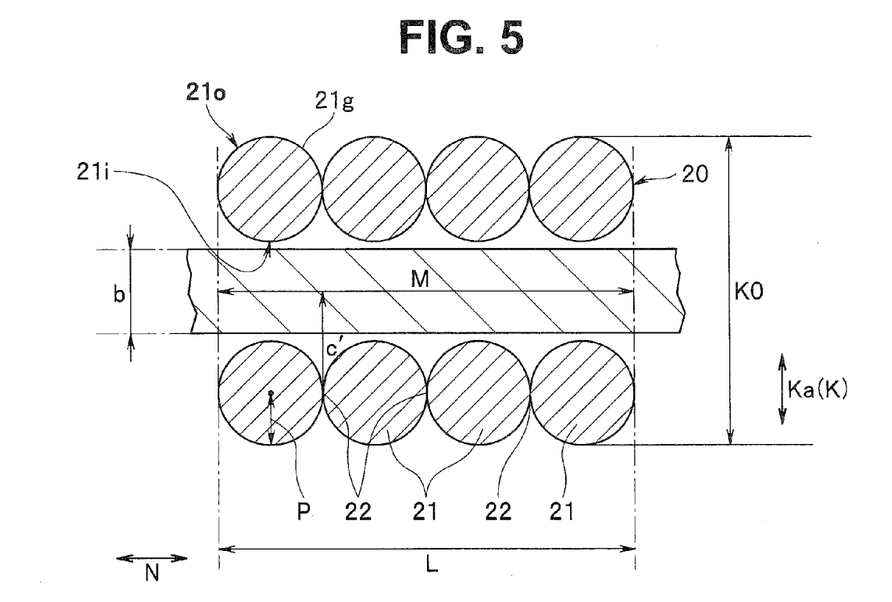
FIG. 5 is a partial cross-sectional view including a coil sheath whose element wire has an exact circle shape in cross section and a longitudinal axis direction of a wire.
Figure 6:
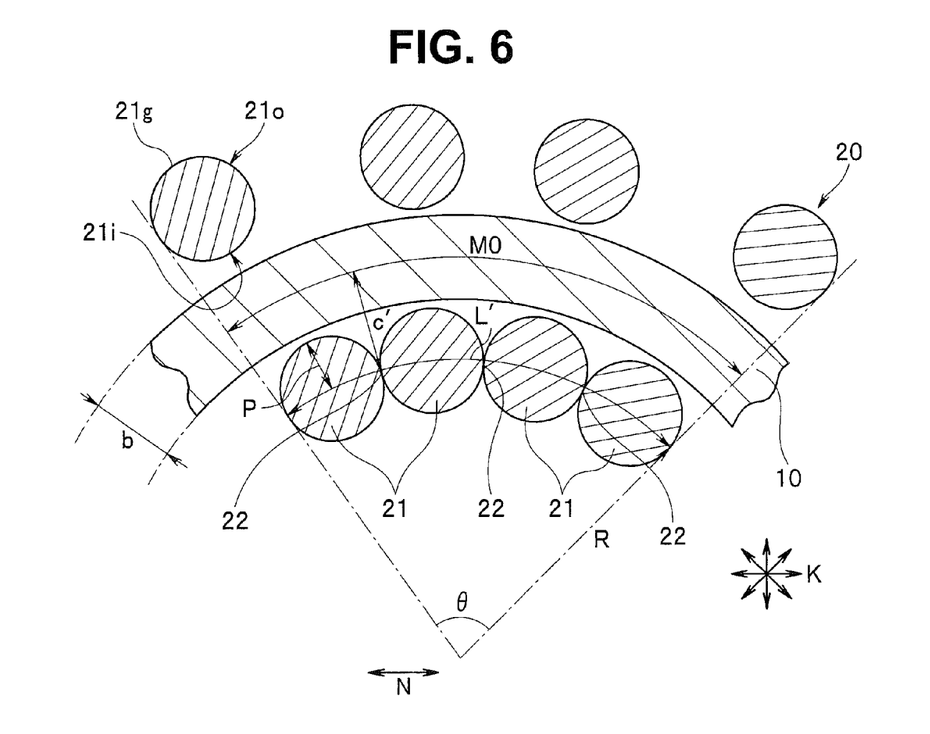
FIG. 6 is a partial cross-sectional view illustrating a state in which the coil sheath in FIG. 5 is bent and the wire is thereby drawn into the coil sheath and including the longitudinal axis direction of the wire.

Also, FIG. 5 is a partial cross-sectional view including a coil sheath whose element wire has an exact circle shape in cross section and a longitudinal axis direction of a wire, and FIG. 6 is a partial cross-sectional view illustrating a state in which the coil sheath in FIG. 5 is bent and the wire is thereby drawn into the coil sheath and including the longitudinal axis direction of the wire.

Note that for simplicity of description of the wires 10r to 10d and a shape of element wires in the coil sheaths 20r to 20d, the wires 10r to 10d and the coil sheaths 20r to 20d are indicated below as a wire 10 and a coil sheath 20. In other words, a configuration indicated by a wire 10 and a coil sheath 20 indicates respective configurations of the wires 10r to 10d and the coil sheaths 20r to 20d.

As illustrated in FIGS. 3 and 4, in the coil sheath 20, an element wire 21 is helically wound along the longitudinal axis direction N.

Each element wire 21 has a shape that allows a line 21s connecting, in the longitudinal axis direction N, contact points 22 between outer peripheral faces 21g of parts of the element wire 21 that are adjacent to one another in the longitudinal axis direction N, to be positioned shifted toward the innermost edge 21*i* side relative to a middle position 21*c* between an outermost edge 21*o* and the innermost edge 21*i* of the outer peripheral face 21*g* of the element wire 21 in one direction Ka perpendicular to the longitudinal axis direction N from among radial directions K in a cross-section including the longitudinal axis direction N.

In other words, each element wire 21 has a shape in which each of the relevant contact points 22 is positioned shifted toward the innermost edge 21*i* side relative to the middle position 21*c*.

Note that at each of the contact points 22, the outer peripheral faces 21*g* of the relevant parts of the element wire 21, the outer peripheral faces 21*g* each having a curved surface, are in contact with each other. In other words, each contact point 22 is provided on a curved surface in the outer peripheral face 21*g* of the relevant parts of the element wire 21.

More specifically, the element wire 21 has a cross-sectional shape of a circle including an innermost edge 21*i* that includes a curved surface and is crushed in the one direction Ka relative to an exact circle with a radius p. Here, the number of contact points 22 between a pair of parts of the element wire 21 that are adjacent to each other in the longitudinal axis direction N, is not limited to one.

Also, examples of a method for forming the outer peripheral face 21*g* of the element wire 21 into the above-described shape include, e.g., molding.

As described above, the present embodiment indicates that the element wire 21 included in the coil sheath 20 has a cross-sectional shape in which each contact point 22 is positioned shifted toward the innermost edge 21*i* side relative to the middle position 21*c* between the outermost edge 21*o* and the innermost edge 21*i* of the outer peripheral face 21*g* of the element wire 21 in the one direction Ka, that is, a cross-sectional shape of a circle including an innermost edge 21*i* that includes a curved surface and is crushed in the one direction Ka relative to an exact circle with the radius p.

According to the above, in comparison to a case where the element wire 21 has a cross-sectional shape of an exact circle with the radius p as illustrated in FIG. 5, the element wire 21 can be disposed with the innermost edge 21*i* close to an outer periphery of the wire 10 having a diameter b. Therefore, a diameter of the coil sheath 20 can be reduced (K1<K0). Thus, a diameter of the flexible tube 2*k* can also be made to be smaller and a distance d from each contact point 22 to a center in the radial direction K of the wire 10 can also be made to be smaller (d<c').

Therefore, when, upon the insertion portion 2 being inserted into a subject, the flexible tube 2*k* passively bends because of a shape inside the subject and the coil sheath 20 also bends as illustrated in FIG. 4, where L is a length in a predetermined area in the longitudinal axis direction N of the coil sheath 20 and M is a length in the longitudinal axis direction N of the wire 10 inserted inside the coil sheath 20 in the length L, as illustrated in FIG. 3, the wire 10 is extended by the amount of M1−M and thus elastically deformed as illustrated in FIG. 4.

More specifically, as described above, a length M1 of the wire 10 after the elastic deformation is $M1=2\pi(R+p1+b/2)\times \theta/360 (p1<p)$, and thus an amount of elastic deformation of the wire 10 can be defined as $M1-L'=\pi\theta(p1+b/2)/180$, and the amount of elastic deformation can be decreased by the amount of decrease from the length M0 of the wire 10 after elastic deformation in the conventional example (M1<M0) as illustrated in FIG. 6, by means of decrease of the distance d relative to a distance c' (d<c') in the case where the element wire 21 has a cross-sectional shape of an exact circle with the radius p as illustrated in FIG. 5.

Therefore, when the wire 10 is pulled in order to bend the bending portion 2*w*, the wire 10 is brought into contact with a part on the inner side in the bending direction of the coil sheath 20; however, as illustrated in FIGS. 5 and 6, tension of the wire 10 can be reduced relative to the case where the element wire 21 has a cross-sectional shape of an exact circle with the radius p.

Therefore, frictional resistance of the wire 10 against the part on the inner side in the bending direction of the coil sheath 20 can be made to be smaller and thus an amount of strength of pulling the wire 10 can be made to be smaller.

Also, as illustrated in FIGS. 3 and 4, the element wire 21 has a sufficient cross-sectional area, that is, thickness and the area of contact between respective parts of the element wire 21 at a contact point 22 remains unchanged compared to the conventional example illustrated in FIGS. 5 and 6, and thus, the element wire 21 is less likely to be displaced in the one direction Ka, that is, a shearing direction and durability of the element wire 21 is enhanced.

According to the above, an endoscope 1 including a configuration in which an amount of elastic deformation of a wire 10 resulting from bending of the flexible tube 2*k*, the wire 10 being inserted inside a coil sheath 20 and bending a bending portion 2*w*, can be made to be smaller than those of the conventional techniques, while element wire displacement in a shearing direction of the coil sheath 20 is prevented can be provided.

(Second Embodiment)

Figure 7:
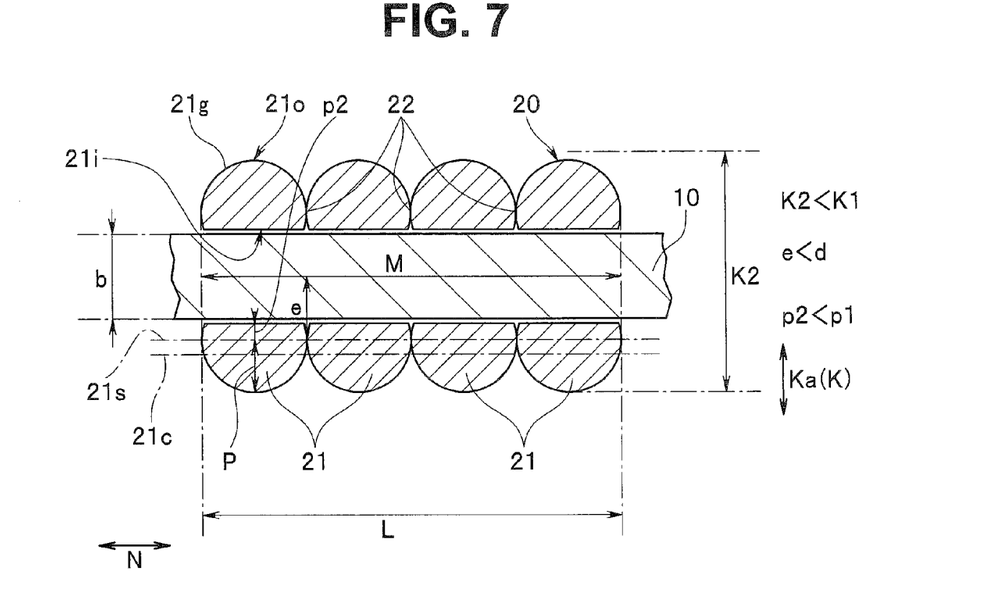
FIG. 7 is a partial cross-sectional view including a coil sheath provided inside an insertion portion of an endoscope according to a second embodiment and a longitudinal axis direction of a wire.
Figure 8:
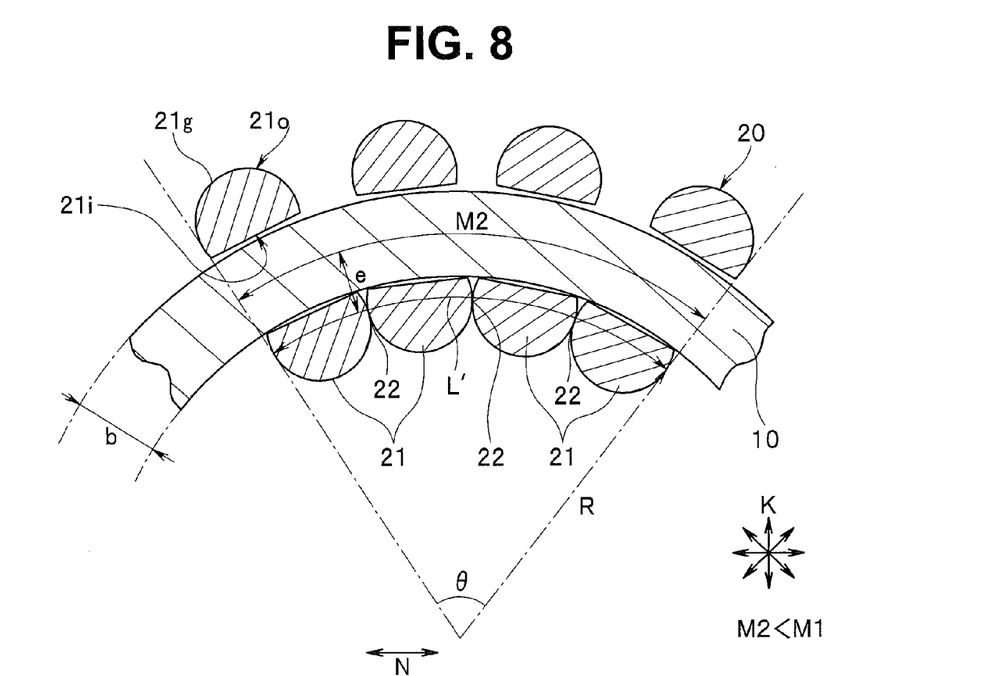
FIG. 8 is a partial cross-sectional view illustrating a state in which the coil sheath in FIG. 7 is bent and the wire is thereby drawn into the coil sheath and including the longitudinal axis direction of the wire.

FIG. 7 is a partial cross-sectional view including a coil sheath provided inside an insertion portion of an endoscope according to the present embodiment and a longitudinal axis direction of a wire, and FIG. 8 is a partial cross-sectional view illustrating a state in which the coil sheath in FIG. 7 is bent and the wire is thereby drawn into the coil sheath and including the longitudinal axis direction of the wire.

A configuration of the endoscope according to the second embodiment is different from that of the endoscope according to the first embodiment illustrated in FIGS. 1 to 4 in that the side of the outer peripheral face on which an innermost edge of an element wire of a coil sheath is positioned is formed so as to include a flat surface. Therefore, only this difference will be described, components that are similar to those of the first embodiment will be provided with reference numerals that are the same as those of the first embodiment and description thereof will be omitted.

As illustrated in FIGS. 7 and 8, in the present embodiment, the side of an outer peripheral face 21*g* of each part of an element wire 21 included in a coil sheath 20 on which an innermost edge 21*i* on one direction Ka is positioned is formed so as to include a flat surface.

Note that examples of a method for making the side of the outer peripheral face 21*g* on which the innermost edge 21*i* is positioned include a flat surface include making the side on which the innermost edge 21*i* is positioned include a flat surface using, e.g., a roller and forming the element wire 21 into the above-described shape by means of molding before the element wire 21 being wound.

Note that the rest of the configuration is the same as that of the first embodiment described above.

According to such configuration as above, the side of the outer peripheral face 21*g* of each part of the element wire 21 on which the innermost edge 21*i* is positioned is formed so as to include a flat surface, and thus a thickness in the one direction Ka of each part of the element wire 21 can be made to be smaller than that of the first embodiment described above, enabling the side on which the innermost edge 21i is positioned to be brought closer to the outer peripheral side of the wire 10.

Thus, a distance e from a contact point 22 to a center in a radial direction K of the wire 10 can be made to be smaller than that of the first embodiment described above (e<d) with the area of contact between parts of the element wire 21 at the contact point 22 secured, the area of contact being the same as that of the above-described first embodiment. Furthermore, a diameter K2 of the coil sheath 20 can be made to be smaller than that of the above-described first embodiment (K2<K1), and thus, a diameter of the flexible tube 2k can also be made to be smaller.

Also, as illustrated in FIG. 8, a length M2 of the wire 10 after elastic deformation is M2=2π(R+p2+b/2)×θ/360 (P2<P1), and thus, the amount of elastic deformation of the wire 10 can be defined as M2−L'=πθ(p2+b/2)/180, and the amount of elastic deformation can be decreased relative to the amount of elastic deformation in the first embodiment by the amount of decrease from the length M1 of the wire 10 after elastic deformation in the first embodiment (M2<M1) as illustrated in FIG. 8 by means of reduction of the distance e relative to a distance d (e<d).

Note that other effects of the present embodiment are the same as those of the first embodiment described above.

(Third Embodiment)

Figure 9:
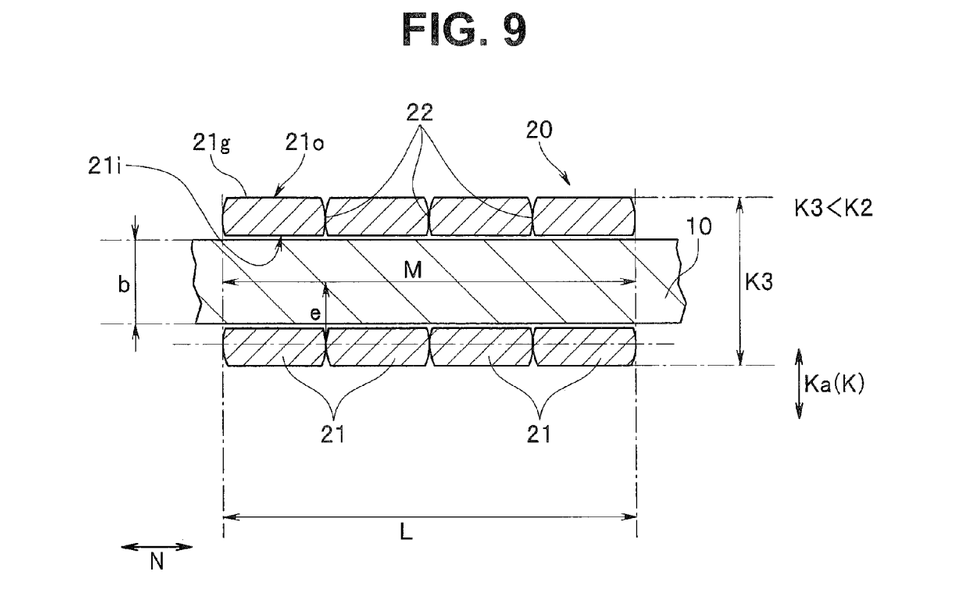
FIG. 9 is a partial cross-sectional view including a coil sheath provided inside an insertion portion of an endoscope according to a third embodiment and a longitudinal axis direction of a wire.
Figure 10:
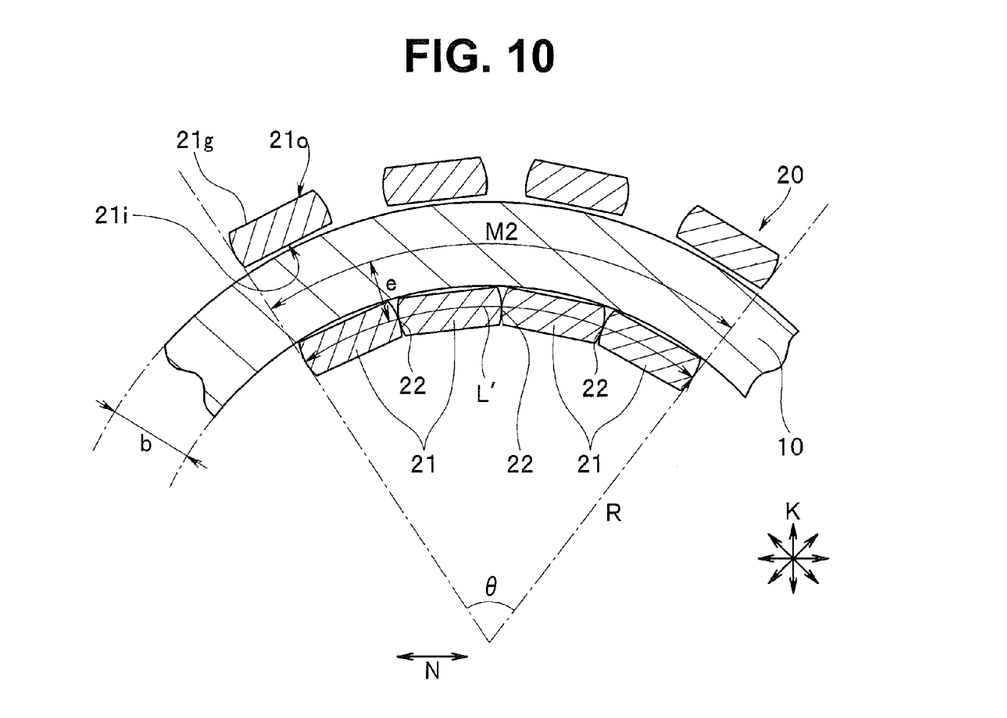
FIG. 10 is a partial cross-sectional view illustrating a state in which the coil sheath in FIG. 9 is bent and the wire is thereby drawn into the coil sheath and including the longitudinal axis direction of the wire.

FIG. 9 is a partial cross-sectional view including a coil sheath provided inside an insertion portion of an endoscope according to the present embodiment and a longitudinal axis direction of a wire, and FIG. 10 is a partial cross-sectional view illustrating a state in which the coil sheath in FIG. 9 is bent and the wire is thereby drawn into the coil sheath and including the longitudinal axis direction of the wire.

A configuration of the endoscope according to the third embodiment is different from the endoscope according to the above-described second embodiment illustrated in FIGS. 7 and 8 in that the side of an outer peripheral face of an element wire in a coil sheath on which an outermost edge is positioned is formed so as to include a flat surface. Therefore, only this difference will be described, components that are similar to those of the second embodiment will be provided with reference numerals that are the same as those of the second embodiment and description thereof will be omitted.

As illustrated in FIGS. 9 and 10, in the present embodiment, as in the second embodiment, the side of an outer peripheral face 21g of each part of an element wire 21 included in a coil sheath 20 on which an innermost edge 21i in one direction Ka is positioned is formed so as to include a flat surface.

Furthermore, the side of the outer peripheral face 21g of each part of the element wire 21 included in the coil sheath 20 on which an outermost edge 21o in the one direction Ka is positioned is formed so as to include a flat surface.

Here, examples of a method for making the side of the outer peripheral face 21g on which the outermost edge 21o is positioned include a flat surface include, as with the side on which the innermost edge 21i is positioned, making the side on which the outermost edge 21o is positioned include a flat surface using, e.g., a roller and forming the element wire 21 into the aforementioned shape by means of molding before the element wire 21 being wound.

Also, the rest of the configuration is the same as that of the above-described second embodiment.

According to such configuration as above, the side of the outer peripheral face 21g of each part of the element wire 21 on which the innermost edge 21i is positioned is formed so as to include a flat surface and the side on which the outermost edge 21o is positioned is also formed so as to include a flat surface, whereby a thickness in the one direction Ka of each part of the element wire 21 is smaller than that of the above-described second embodiment. Thus, a diameter K3 of the coil sheath 20 can be made to be smaller than that of the above-described second embodiment (K3<K2), and thus a diameter of a flexible tube 2k can also be made to be smaller.

Note that other effects of the present embodiment are the same as those of the above-described second embodiment.

Also, in the present embodiment, it is possible that, at least, only the side of the outer peripheral face 21g of each part of the element wire 21 included in the coil sheath 20 on which the outermost edge 21o in the one direction Ka is positioned is formed so as to include a flat surface.

In other words, the side of the outer peripheral face 21g of each part of the element wire 21 included in the coil sheath 20 on which the innermost edge 21i in the one direction Ka is positioned may be formed so as to include no flat surface.

(Fourth Embodiment)

Figure 11:
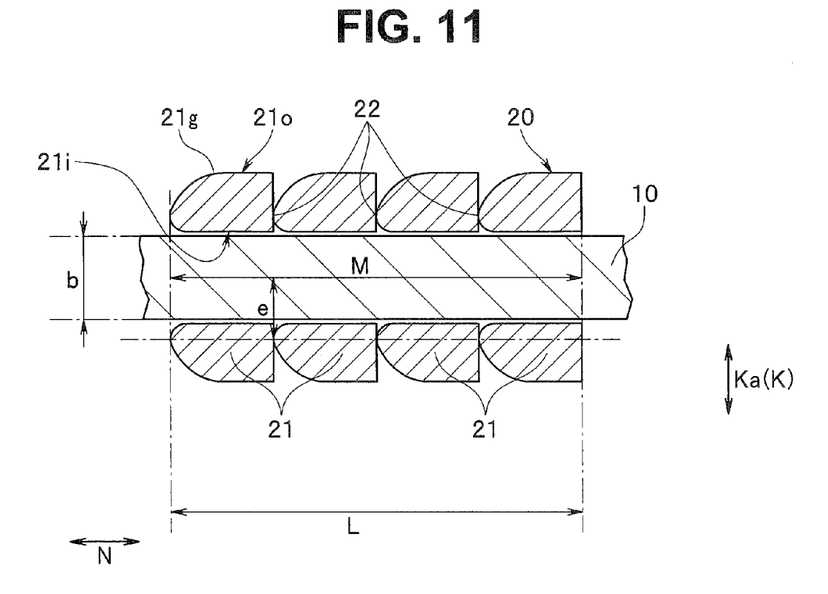
FIG. 11 is a partial cross-sectional view including a coil sheath provided inside an insertion portion of an endoscope according to a fourth embodiment and a longitudinal axis direction of a wire.
Figure 12:
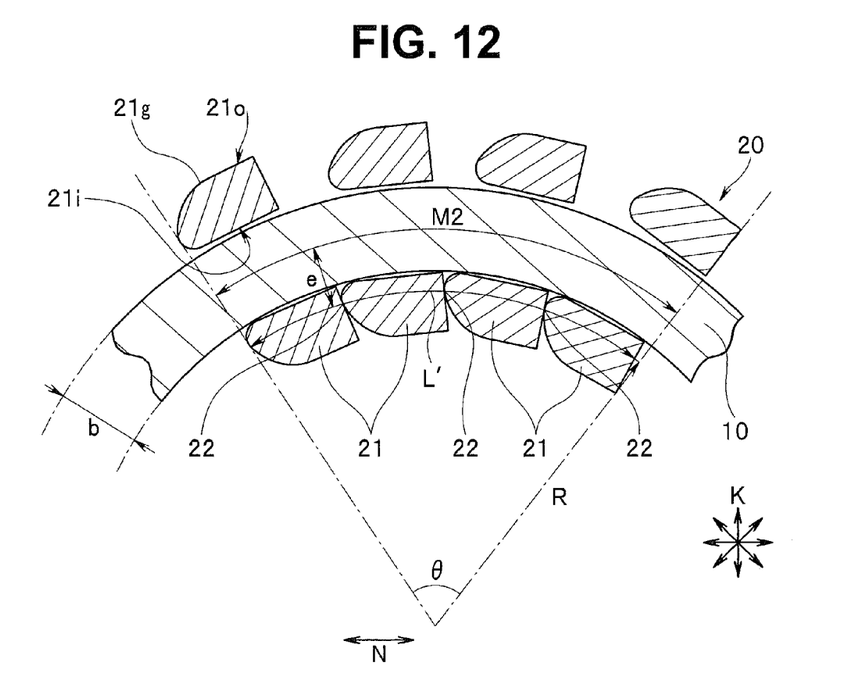
FIG. 12 is a partial cross-sectional view illustrating a state in which the coil sheath in FIG. 11 is bent and the wire is thereby drawn into the coil sheath and including the longitudinal axis direction of the wire.

FIG. 11 is a partial cross-sectional view including a coil sheath provided inside an insertion portion of an endoscope according to the present embodiment and a longitudinal axis direction of a wire, and FIG. 12 is a partial cross-sectional view illustrating a state in which the coil sheath in FIG. 10 is bent and the wire is thereby drawn into the coil sheath and including the longitudinal axis direction of the wire.

A configuration of the endoscope according to the fourth embodiment is different from that of the endoscope according to the above-described third embodiment illustrated in FIGS. 9 and 10 in that at a contact point between parts of an element wire in a coil sheath, one of the parts is formed so as to include a flat surface. Therefore, only this difference will be described, components that are similar to those of the third embodiment will be provided with reference numerals that are the same as those of the third embodiment and description thereof will be omitted.

Each of the above-described first to third embodiments indicates that the outer peripheral faces 21g of the respective parts of the element wire 21, the outer peripheral faces 21g each including a curved surface, are in contact with one another at the respective contact points 22, that is, each contact point 22 is provided on a curved surface of the outer peripheral face 21g of each part of the element wire 21.

The present invention is not limited to this configuration, and as illustrated in FIGS. 11 and 12, it is possible that a contact point 22 on one of adjacent parts of an element wire 21 is provided on a flat surface.

Note that the rest of the configuration is the same as that of the above-described third embodiment. Also, both of the sides of an outer peripheral face 21g of the element wire 21 on which an innermost edge 21i and an outermost edge 21o in one direction Ka is positioned may be formed so as to include no flat surface.

Also, examples of a method for forming a shape of the outer peripheral face 21g of the element wire 21 into the above-described shape include, e.g., molding.

According to such configuration as above, when a flexible tube 2k is bent, a coil sheath 20 smoothly bends, and even if parts of the element wire 21 are displaced from each other in a shearing direction, a contact point 22 on one of the adjacent parts of the element wire 21 is provided on a flat surface. Therefore, the contact point 22 provided on a curved surface of the other of the adjacent parts is merely displaced in the shearing direction, and thus no variation occurs in total length in a longitudinal axis direction N of the coil sheath 20.

This is because in contact between contact points 22 both provided on curved surfaces, when relevant parts of the element wire 21 are displaced from each other in the shearing direction, the contact point 22 on one of the parts of the element wire 21 moves along a shape of the curved surface in an outer peripheral face 21g of the other part of the element wire 21 and a total length of the coil sheath 20 is decreased in the longitudinal axis direction N by the amount of the movement.

Note that other effects of the present embodiment are the same as those of the above-described third embodiment.

Also, although each of the above-described first to fourth embodiments has been described taking an endoscope 1 as an example of a medical device, the present invention is not limited to this example, and it should be understood that the present invention is applicable even to a treatment instrument including a coil sheath and a wire inside a flexible tube and including a grasping portion to be actuated upon the wire being pulled, such as a manipulator that can be inserted into a channel in an endoscope.

What is claimed is:

1. An endoscope comprising:
    a bendable bending portion;
    a coil sheath including a single element wire helically wound in a longitudinal axis direction to define an interior; and
    a wire disposed in the interior of the coil sheath, the wire being pulled for bending the bending portion;
    wherein an outer peripheral face of the single element wire is formed to have a curved face on one side of the outer peripheral face and to have a flat surface along a shearing direction perpendicular to the longitudinal axis direction of the single element wire on another side of the outer peripheral face; and
    the coil sheath is wound such that the curved face of one winding of the single element wire and the flat surface of an adjacent winding of the single element wire are in contact with each other.

2. The endoscope according to claim 1, wherein:
    the curved face of the one winding and the flat surface of the adjacent winding are in contact with each other at a contact point; and
    the contact point is positioned closer to the interior of the coil sheath than an outermost periphery of the coil sheath.

3. The endoscope according to claim 2, wherein the single element wire is formed so that a part of the outer peripheral face, in which the interior in the radial direction is positioned.

4. The endoscope according to claim 2, wherein the single element wire is formed such that a part of the outer peripheral face in which the outermost edge in the radial direction is positioned includes a flat surface.

5. The endoscope according to claim 1, further comprising a flexible tube, a distal end of the flexible tube, in the longitudinal axis direction, is coupled with the bending portion, the flexible tube having flexibility, and the wire and the coil sheath being disposed within the flexible tube.

6. The endoscope according to claim 1, further comprising an operation input section that pulls the wire.

7. An insertion section for use with an endoscope, the insertion section comprising:
    a bendable bending portion;
    a coil sheath including a single element wire helically wound in a longitudinal axis direction to define an interior; and
    a wire disposed in the interior of the coil sheath, the wire being pulled for bending the bending portion;
    wherein an outer peripheral face of the single element wire is formed to have a curved face on one side of the outer peripheral face and to have a flat surface along a shearing direction perpendicular to the longitudinal axis direction of the single element wire on another side of the outer peripheral face; and
    the coil sheath is wound such that the curved face of one winding of the single element wire and the flat surface of an adjacent winding of the single element wire are in contact with each other.

* * * * *